United States Patent
Fulle et al.

(10) Patent No.: US 9,165,844 B2
(45) Date of Patent: Oct. 20, 2015

(54) EXAMINATION OF A SILICON SUBSTRATE FOR A SOLAR CELL

(71) Applicant: SOLARWORLD INNOVATIONS GMBH, Freiberg (DE)

(72) Inventors: Alexander Fulle, Wilkau-Hasslau (DE); Andreas Krause, Radebeul (DE); Lamine Sylla, Dresden (DE)

(73) Assignee: SOLARWORLD INNOVATIONS GMBH, Freiberg (DE)

( * ) Notice: Subject to any disclaimer, the term of this patent is extended or adjusted under 35 U.S.C. 154(b) by 39 days.

(21) Appl. No.: 13/941,910

(22) Filed: Jul. 15, 2013

(65) Prior Publication Data
US 2014/0038316 A1 Feb. 6, 2014

(30) Foreign Application Priority Data
Aug. 3, 2012 (DE) .................. 10 2012 213 793

(51) Int. Cl.
| | |
|---|---|
| *H01L 21/00* | (2006.01) |
| *G01R 31/26* | (2014.01) |
| *H01L 21/66* | (2006.01) |
| *G01N 21/59* | (2006.01) |
| *G01N 21/95* | (2006.01) |
| *G01N 21/84* | (2006.01) |

(52) U.S. Cl.
CPC .............. *H01L 22/24* (2013.01); *G01N 21/59* (2013.01); *G01N 21/95* (2013.01); *G01N 21/9505* (2013.01); *G01N 2021/8477* (2013.01); *H01L 2924/0002* (2013.01)

(58) Field of Classification Search
CPC ... G01N 21/59; G01N 21/95; G01N 21/9505; G01N 21/2026; H01L 29/78696; H01L 29/66765; H01L 29/78678; H01L 29/04

USPC .......... 438/14, 16, 17, 18, 166, 487; 257/347, 257/352, 507, 521, 627, 66, 72, E33.003, 257/E31.04, E29.003, E29.105, E29.286, 257/E29.294, E21.134, E21.414, E21.345; 358/326, 432; 117/85, 55

See application file for complete search history.

(56) References Cited

U.S. PATENT DOCUMENTS

| | | | |
|---|---|---|---|
| 7,920,738 B2 | 4/2011 | Sauar et al. | |
| 2007/0141734 A1* | 6/2007 | Flynn | 438/16 |
| 2007/0215877 A1* | 9/2007 | Kato et al. | 257/66 |
| 2007/0249085 A1* | 10/2007 | Ojima et al. | 438/64 |
| 2008/0153186 A1* | 6/2008 | Saito et al. | 438/16 |
| 2010/0253942 A1* | 10/2010 | Mack et al. | 356/326 |
| 2011/0045612 A1* | 2/2011 | Kelman et al. | 438/7 |
| 2012/0272944 A1* | 11/2012 | Coustier et al. | 125/21 |
| 2013/0244369 A1* | 9/2013 | Nishimoto et al. | 438/71 |

FOREIGN PATENT DOCUMENTS

| | | |
|---|---|---|
| CN | 101573801 A | 11/2009 |
| DE | 11 2005 000 410 T5 | 1/2007 |
| DE | 20 2009 017 691 U1 | 6/2010 |

\* cited by examiner

*Primary Examiner* — Julio J Maldonado
*Assistant Examiner* — Moazzam Hossain
(74) *Attorney, Agent, or Firm* — Oliff PLC

(57) ABSTRACT

The invention relates to a method for examining a wire-sawn silicon substrate for a solar cell. The method includes irradiating the silicon substrate with an infrared radiation, detecting the infrared radiation transmitted through the silicon substrate, and analyzing the detected infrared radiation for characterizing the crystal orientation of the silicon substrate. The invention in addition relates to a device for carrying out such a method, and a method for manufacturing a solar cell.

10 Claims, 7 Drawing Sheets

EXAMINATION OF A SILICON SUBSTRATE FOR A SOLAR CELL

The present invention relates to a method for examining a wire-sawn silicon substrate for a solar cell. In addition, the invention relates to a device for carrying out such a method, and a method for manufacturing a solar cell.

Solar cells are employed for converting the electromagnetic radiation energy, particularly sunlight into electrical energy. Conventional Solar cells are manufactured from the base material silicon. Therefore, a block (or also bar) is produced from silicon, which is split into disc-shaped silicon substrates, also referred to as wafer. Here, generally a wire sawing process is used. The substrates produced in this manner are subjected to further processes, in which inter alia a surface texture, a p-n junction, an anti-reflection coating, and contact structures are configured. The surface texture serves to facilitate an improved radiation input into the substrate of a solar cell.

Solar cells can be configured with polycrystalline or monocrystalline silicon substrates. Monocrystalline cells have a high efficiency and can have surface texture with pyramid structures produced by an alkaline etching process. Such a texture which is characterized by a low reflectivity and high input efficiency can be produced by the presence of a surface with a 100-crystal orientation.

Carrying out a casting process for manufacturing a silicon block for substrates having high monocrystalline aggregate with 100-orientation has increasingly gained importance in the recent years. Here, one or several monocrystalline seeds are laid at the bottom of a mould and covered with silicon material. The material is melted insofar as from above that the seed/seeds are only slightly melted. The subsequent directional solidification takes place on the still unmolten seed patterns. By the presence of seed joints (seeds bordering on each other) and a parasitic crystallization on the mould wall, a multi crystals growth with diverging crystal orientation may occur. Therefore, the substrates sawn from a casted silicon block generally have a multicrystalline aggregate on the surface. Here, the consequence of carrying out an alkaline process has the effect that multicrystalline regions are not textured and the substrates can have a blotchy appearance. Indeed it is possible to carry out an acidic texturing replete with alkaline, whereby even regions with a diverging crystal orientation are textured. However, the texture produced in this offers a lower input efficiency.

For this reason, it is strived to characterize the crystal orientation of a silicon substrate. Thereby, it is possible for example, to provide an aggregate of 100-crystal orientation for monocrystalline substrates, at which a alkaline or acidic texturing is carried out. The known procedure consists of irradiating a silicon substrate with visible light and to produce an incident light image. In the incident light image, the largest surface with a uniform brightness is determined and measured. This surface is equated with a grain having 100-crystal orientation, the aggregate of which is determined with respect to the total substrate surface. However, the aggregate of the largest grain (alone) is not decisive for the efficiency of a solar cell. Further smaller grains may be available with 100-crystal orientation, which can likewise be textured alkaline. It is also possible that a grain is identified with a different crystal orientation than the largest grain, whereby a wrong aggregate of the 100-crystal orientation is determined. This case may occur, for example in substrates which emerge from a peripheral zone of a silicon block. Further, it may occur that a silicon substrate has two separated, relatively larger grains with 100-crystal orientation, because of the seed joints or twin growth. Here, only one of these grains is considered, whereby a to small aggregate of the 100-orientation is determined.

The object of the present invention consists of specifying a solution for an improved examination of a silicon substrate for a solar cell. It is a further object of the invention to specify a method for manufacturing a solar cell, within the scope of which such an examination is carried out.

This object is achieved by the features of the independent patent claims. Further advantageous embodiments of the invention are specified in the dependent claims.

In accordance with the invention, a method is proposed for examining a wire-sawn silicon substrate for a solar cell. The method comprises irradiating the silicon substrate by an infrared radiation, detecting the infrared radiation transmitted through the silicon substrate and evaluating the detected infrared radiation for characterizing crystalline orientation of the silicon substrate.

In contrast to the conventional methods of examination, in which for example, the incident light images or even the images by means of photoluminescence are used, the examination of the silicon substrate proposed in the method here, takes place by irradiating the substrate with infrared radiation and detecting the transmitted radiation. Here, the radiation, particularly the intensity of the radiation can be detected in a spatially resolved manner. The characterization is based on that the infrared radiation undergoes a different attenuation or absorption while passing through the substrate depending on the every available crystal orientation. The different attenuation or absorption capacity is based on that, due to the wire sawing taken place before the examination, the silicon substrate has different saw damage dependent on the respective crystal orientation. This effect is used for characterizing a definite crystal orientation present on the surface (or on the main surfaces) of the silicon substrate. The crystal orientation can be differentiated particularly from other crystal orientations, whereby the information about the relevant crystal orientation can be obtained, and a reliable and accurate assessment is possible.

In a preferred embodiment, the evaluation refers to determining an aggregate of the surface of the silicon substrate by the crystal orientation to be characterized. Therefore, the overall surface aggregate of the crystal orientation, and not just the aggregate of the largest grain, is determined. The surface aggregate can be considered insofar as, for example to define the further processing of the wire-sawn substrate. It is further possible, for example to recognize a flawless supply of the wire-sawn silicon substrate.

Preferably, the radiation of the near infrared region is used in the method. For example, the use of infrared radiation with wavelengths in the range of 800 nm to 1200 nm is taken into account. In this manner, it can be achieved that differences in the radiation absorption or attenuation, caused by the crystal orientation dependent saw damages are relatively large. Because of this, an accurate examination can be favored.

The different, absorption or attenuation of the infrared radiation dependent on the respective crystal orientations means that while detecting the transmitted infrared radiation, different radiation intensities can be measured. In this respect, it is provided according to another preferred embodiment to form the frequency distribution of different intensities (or brightnesses) of the detected infrared radiation with regard to an aggregate of the silicon substrate. Based on the frequency distribution, the characterization, particularly determining the aggregate of a defined crystal orientation on the substrate surface can be carried out with a higher speed and accuracy. The frequency distribution can be represented in form of a histogram within the scope of the evaluation.

In another preferred embodiment, in which in particular, the above mentioned frequency distribution can be used, the total frequency with regard to the surface of the silicon substrate is determined from different intensities of the detected infrared radiation. The total frequency may refer to all the possible crystal orientations of the silicon substrate. Further, another frequency of intensities of the detected infrared radiation is determined, which are associated (merely) with the regions of the silicon substrate having the crystal orientation to be characterized. In addition, the ratio is formed from the other frequency and the total frequency. This ratio corresponds to the overall aggregate of the surface of the silicon substrate having the crystal orientation to be characterized.

In another preferred embodiment, in which the saw damage dependent and thereby crystal orientation dependent radiation absorption or attenuation is used, an association between the crystal orientation to be characterized and the intensities of the detected infrared radiation takes place. In this manner, the measured radiation intensities can be linked to the regions of the silicon substrate with the relevant crystal orientation.

In another preferred embodiment, the association takes place by means of the above mentioned frequency distribution from different intensities of the detected infrared radiation. Therefore, it is provided to carry out the association on the basis of a peak value or peaks in the frequency distribution. For example, it can be used that a peak related to the crystal orientation comes to lie on the same (at least relatively) position or in the region of the same or corresponding intensities of the frequency distribution.

In particular, this characteristic can also be used to determine the above mentioned other frequency of radiation intensities, which are merely associated with the regions of the silicon substrate having the crystal orientation to be characterized. The requested frequencies can be determined by carrying out a peak search about the relevant intensity range of the frequency distribution, a peak deconvolution process for separating the peak, and integrating the frequency of the separated peak. The total frequency referring to all the crystal orientations can be determined by adding up all the frequencies of the frequency distribution or by integrating the overall frequency distribution.

In another preferred embodiment, the association between the crystal orientation and the detected radiation intensities can be carried out on the basis of a calibration measurement. In the calibration measurement, for example a monocrystalline wire-sawn reference substrate or a part of such a substrate can be measured, in which the presence of the relevant crystal orientation is known or can be assumed. The measurement takes place in the above mentioned manner, i.e. by irradiating the reference substrate with infrared radiation and detecting the transmitted infrared radiation. Because of this, the reliability and accuracy of the evaluation can be favored.

If necessary, it may be considered to use both methods of association together in order to achieve a higher reliability. For instance, the above described determination of the other frequency can be favored, when the peak search is carried out or verified based on the calibration measurement.

A transmission image of the examined silicon substrate can also be generated and represented from the detected infrared radiation within the scope of the evaluation. In the transmission image, different detected radiation intensities with different colours or brightnesses can be represented in a spatially resolved manner. For example, it is possible to compile the above mentioned frequency distribution on the basis of the transmission image.

Apart from the surface aggregate of the crystal orientation to be characterized, the evaluation may also refer to other characteristics. In this respect, it is provided according to another preferred embodiment, to determine a spatial distribution of the crystal orientation over a surface of the silicon substrate. Even on the basis of this, for example, the further processing of the wire-sawn substrate can be predefined, or for example, a flawless supply of the substrate can be recognized.

The spatial distribution can be represented, for example in the form of a modified transmission image. Therefore, radiation intensities which are linked to the relevant crystal orientation or are linked in the above described manner (i.e. evaluating a peak value and/or calibration measurement), can be highlighted from other radiation intensities. For instance, the radiation intensities linked to the crystal orientation can be represented by a first brightness (for instance, white) and other radiation intensities with a second brightness (for instance, black). A representation in different colours is also possible.

In another preferred embodiment, the method for examining a silicon substrate which has a monocrystalline crystal structure is used. Here, in the crystal orientation to be characterized, it concerns a 100-crystal orientation. In this respect, the silicon substrate may relate to a casted silicon block developed by splitting or by wire-sawn silicon substrate. The silicon block may be produced by means of a casting process using one or several monocrystalline seeds.

With respect to a crystal orientation mentioned here, it is pointed out that here all crystallographically equivalent orientations are included (thus for 100-crystal orientation also, for example—the 010- and the 001-crystal orientation).

It is further possible to examine a polycrystalline silicon substrate and/or others, instead of a monocrystalline substrate, and if necessary, to characterize even more crystal orientations. For providing a polycrystalline silicon substrate for a solar cell, an underlying silicon block can be produced by a directed solidification of molten silicon without seed specification, which is split or wire-sawn. For a polycrystalline silicon substrate, for example, it may be considered to characterize a 111-crystal orientation in order to evaluate the casting process based on this.

In addition, in accordance with the invention, a device is proposed which is configured for carrying out the above described method or one of the above described embodiments. The device has an irradiation device for irradiating a wire-sawn silicon substrate for a solar cell with an infrared radiation. Further, the device has a detection device for detecting infrared radiation (particularly near infrared radiation) transmitted through the silicon substrate, and an evaluation device for evaluating the detected infrared radiation, in order to characterize a crystal orientation of the silicon substrate. The saw damage dependent effects of the infrared radiation are used in the device in order to characterize the crystal orientation of the substrate in a reliable and accurate manner.

In a preferred embodiment, the evaluation device is configured to form a frequency distribution of different intensities of the detected infrared radiation with regard to the surface of the silicon substrate, and to determine a surface aggregate of the silicon substrate by the crystal orientation on the basis of the frequency distribution. On the basis of the frequency distribution, the determination of the surface aggregate can take place with a higher speed and accuracy.

In addition, in accordance with the invention, a method for manufacturing a solar cell is proposed. A wire-sawn silicon substrate is provided by the method. The provided silicon substrate is examined by carrying out the above described method of examination or one of the described embodiments of the method is used. Depending on the examination of the silicon substrate, a surface texture of the silicon substrate is configured by carrying out an alkaline etching process or by carrying out an acidic etching process. For example, it is possible to determine a surface aggregate of 100-crystal orientation and to compare this with a predefined limiting value. Depending on the comparison, the substrate can be subjected to an alkaline or acidic etching process. The limiting value considered here can be, for example, a surface aggregate of 80%. Depending on the result of the examination or for example, by a comparison with another (smaller) limiting value, it may be considered to sort out the relevant substrate, and therefore, not to process further.

The previously explained features and/or the instructions and improvements of the invention referred to in the subordinate claims may—except for example in cases of explicit dependencies or inconsistent alternatives—are applicable individually or also in any combination with each other.

The invention is explained in the following with the help of figures in more details. They show.

Figure 1:
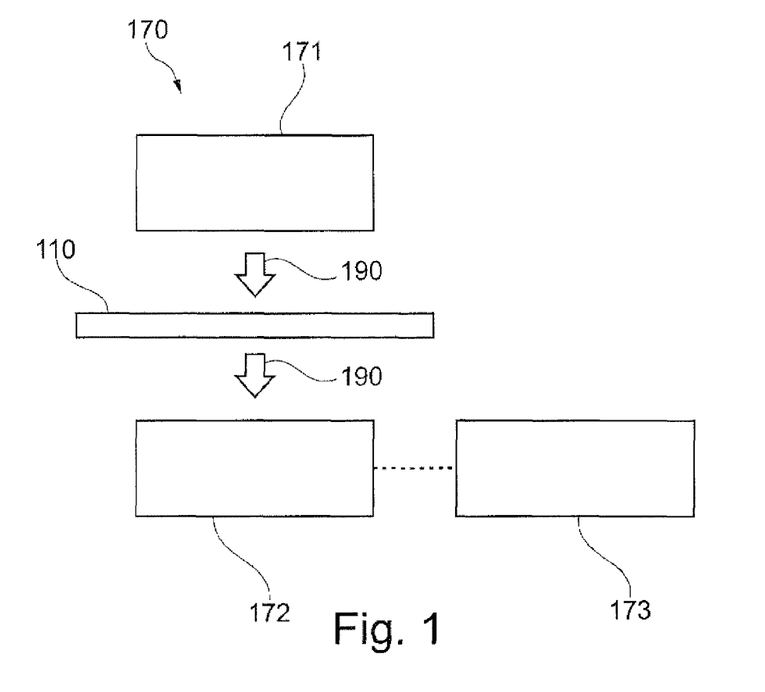
FIG. 1 shows a schematic representation of a device for examining a wire-sawn silicon substrate for a solar cell.

FIG. 1 shows its schematic representation of a device 170, whereby a wire-sawn silicon substrate 110 can be examined within the scope of a solar cells manufacturing. The device 170 is configured for characterizing the crystal orientation of silicon substrate 110. Steps of a method of examination that can be carried out with the help of the device 170, which can be simultaneously or substantially simultaneously carried out, are additionally summarized in the flow diagram of FIG. 2. Silicon substrate 110 can have a monocrystalline crystal structure, wherein a 100-crystal orientation may be present on the main surfaces (i.e. on the front side 111 and on the rear side 112, compare FIG. 10).

Such a wafer 110 can be produced by casting process and a silicon block having a (predominantly) monocrystalline structure may follow (not represented). The casting process includes crystallization of molten silicon in a mould by using one or several monocrystalline seeds at the bottom of the mould, wherein the seed or the seeds are not completely molten during the melting of the silicon. In contrast to otherwise usual Czochralski Drawing method, the casting method, which is also referred to as Quasi-Mono method, offers advantages as for example a lower effort and lower costs.

The silicon block developed in this manner and having a (predominantly) monocrystalline structure is cut by a band- or wire saw in smaller pillar shaped blocks. These blocks are split by a wire saw into separate substrates 110. In the wire saw, a slurry referred to as suspension made of a liquid carrier, and sawing particles and a wire are used. The wire can be stretched in the form of a wire web. The wire moves during the wire sawing, whereby the silicon can be sawn by means of abrasively acting sawing particles.

Silicon substrate 110 produced in this manner and to be examined by means of the device 170, may further involve a so-called vertical wafer. Here, the molten silicon block is divided, perpendicular to the direction of growth which is present during the casting method, into the so-called horizontal pillars. The pillars are again sawn in substrate 110 perpendicular to the direction of growth. Here, the casting or developing the silicon block can take place on a seed surface with 110-orientation.

Silicon substrate 110 to be examined can be configured with 100-crystal orientation, as described above, on the main surfaces. In addition, even an aggregate with other crystal orientations or a multicrystalline aggregate may be present. This is caused by disturbances in the crystal growth during the casting process. Possible reasons are, for example, seed joints (seeds bordering on each other), a parasitic crystallization on the mould wall, and a twin growth.

Figure 10:
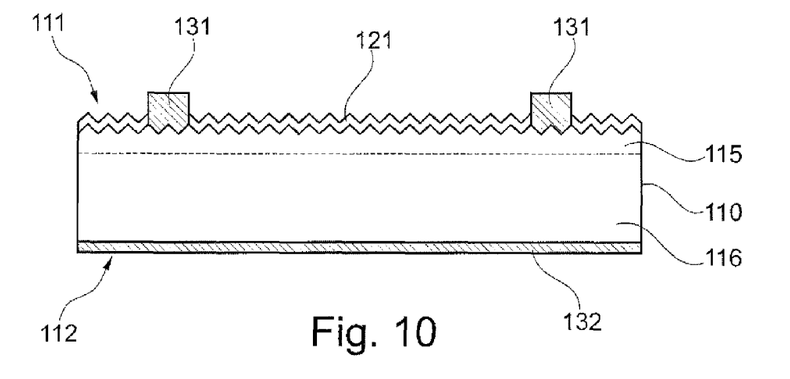
FIG. 10 shows a schematic lateral representation of a solar cell.

Within the scope of further processing of the wire-sawn silicon substrate 110 to a solar cell 100, conventionally a surface texture is produced (compare FIG. 10 with the textured front side 111). In this manner, an improved radiation input can be obtained in operation of the solar cell 100. The texturing can take place in different manners.

A surface with 100-crystal orientation can be structured by an alkaline etching process by using lye, wherein pyramid structures are produced. Such a texture is characterized by a low reflectivity and thereby a high input efficiency. But, the disadvantage is that regions with a different crystal orientation are not structured alkaline. Depending on the aggregate, differently oriented or multicrystalline regions, this may lead to reduction in the efficiency of the solar cell 100. The solar cell 100 may have even a blotched physical appearance.

In order to texture substrate 110 as uniformly as possible, an etching process by using an acid can also be carried out. Thereby, even regions with other crystal orientations obtain a texture. The acid produced texture however has a lower efficiency than the alkali produced texture.

For this reason, it is strived to accurately characterize 100-crystal orientation in substrate 110 produced by casting and sawing, in order to define further processing of substrate 110 based on this. For example, it is considered to determine an aggregate or surface aggregate of silicon substrate 110 with 100-crystal orientation. In addition, it may be provided to obtain further information, for instance about the spatial distribution of 100-crystal orientation.

The device 170 employed for this purpose is configured to carry out an examination of the wire-sawn silicon substrate 110 in the transmission mode with infrared radiation 190 of the near infrared region. For example, wavelengths falling within the range of 800 nm to 1200 nm can be considered for the infrared radiation 190. In the device 170 and the method carried out by device 170 is based on that, during the passage through the substrate 110 depending on the crystal orientations present, the used infrared radiation 190 is attenuated or absorbed to different degrees. The different attenuation is based on that the substrate 110 has saw damages on the main sides (front side 111, rear side 112) due to wire sawing, wherein the saw damages are differently pronounced depending on the crystal orientation. The different crystal orientation dependent saw damages cause a different attenuation of the penetrating infrared radiation 190, which is relatively distinctly pronounced in the near infrared region. Thereby, it is possible to differentiate a specific crystal orientation, presently the 100-orientation, of substrate 110 afflicted with the saw damage from other crystal orientations, so that the relevant crystal orientation can be characterized in a reliable and accurate manner.

Figure 2:
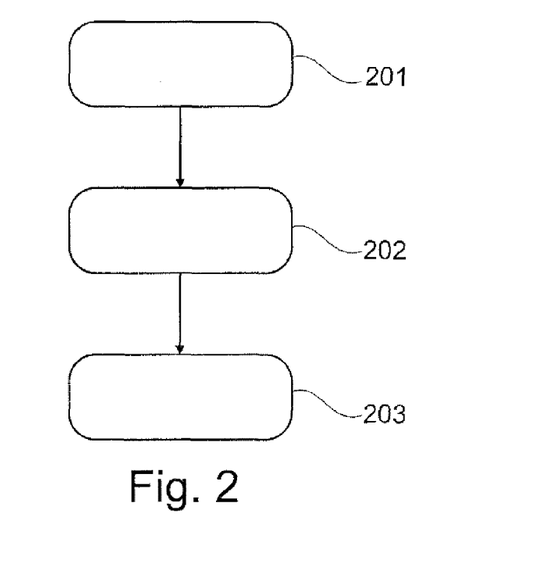
FIG. 2 shows a flow diagram of a method for examining a wire-sawn silicon substrate for a solar cell.

The device 170 has, as shown in FIG. 1, an irradiation device 171, whereby silicon substrate 110 or a main surface of the same can be irradiated with infrared radiation 190 (step 201 in FIG. 2). In addition, device 170 has a detection device 172, whereby the aggregate of the infrared radiation 190 transmitted through substrate 110 and leaving at the other or opposite main surface can be detected in a spatially resolved manner (step 202 in FIG. 2). The radiation intensity of transmitted radiation 190 can be measured by means of detection device 172. Therefore, infrared radiation 190 directly passing through substrate 110 can be respectively measured (bright field exposure to light).

The irradiation device 171 can be configured, for example to irradiate silicon substrate 110 over its entire surface. In the same manner, the detection device 172 can be configured for surface detection of the entire infrared radiation 190 passing substrate 110. However, it is also possible that irradiation device 171 is configured for a section-by-section, particularly for a line-by-line irradiation of silicon substrate 110. In the same manner, the detection device 172 can be provided for detecting the transmitted radiation 190 section-by-section or line-by-line. In order to facilitate the penetration of the entire substrate surface and detection of infrared radiation 190 passing the entire substrate surface, even during a section-by-section irradiation and/or detection, it is provided in such arrangements to accordingly move substrate 110, one of the two devices 171, 172 and/or both devices 171, 172. For instance, both devices 171, 172 may be stationary, and substrate 110 may be laterally moved with the help of a suitable retention device.

The irradiation device 171 can include, for example one or multiple halogen lamps configured for emitting infrared radiation 190. In another possible arrangement, irradiation device 171 may include, for example an arrangement made of electroluminescent diodes (LEDs) emitting infrared radiation 190. The corresponding detection device 172 can be configured, for example in the form of a suitable camera or in the form of a corresponding detector arrangement. In addition, detection device 172 may include an optical filter in order to merely detect radiation 190 from the (Near-) infrared region provided.

The device 170 additionally has, as shown in FIG. 1, an evaluation device 173, whereby detected transmitted infrared radiation 190 can be analyzed (step 203 in FIG. 2). Within the scope of the analysis, it is provided to characterize a specific crystal orientation of the wire-sawn silicon substrate 110, presently the 100-crystal orientation.

One such characterization, which can be carried out with the help of evaluation device 173 within the scope of the step 203 is explained in more details in the following by means of two examined silicon substrates 110. The supply of this substrate 110 took place in the above described manner (i.e. by casting, followed by splitting or wire sawing), so that the main surfaces have 100-crystal orientation.

Figure 3:
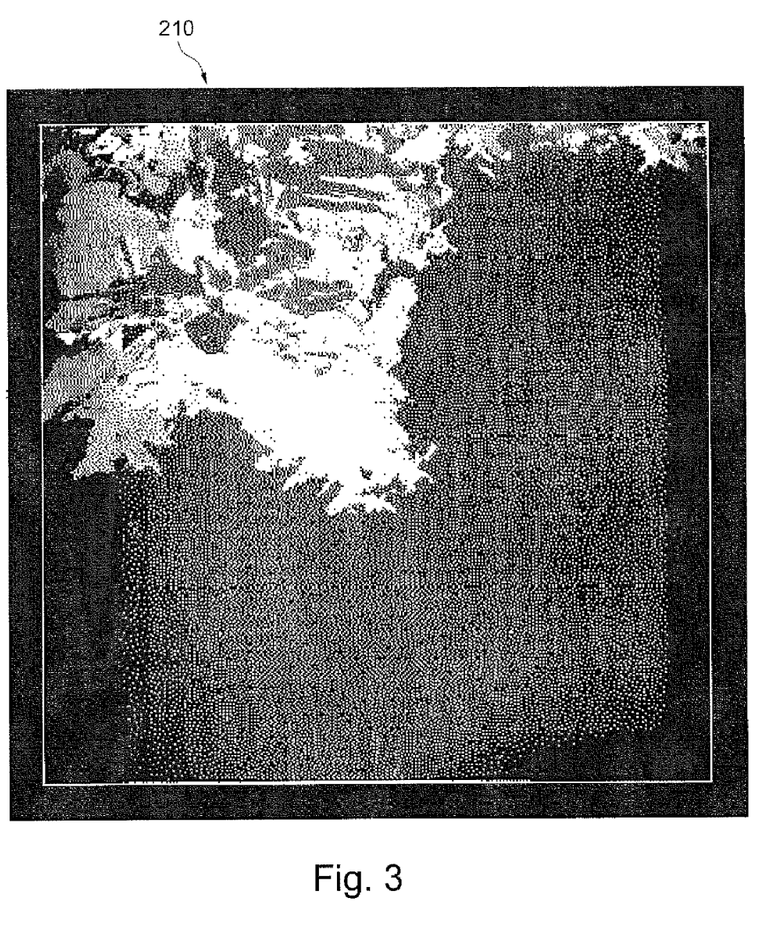
FIG. 3 shows a transmission image generated by penetrating a wire-sawn silicon substrate with an infrared radiation.
Figure 4:
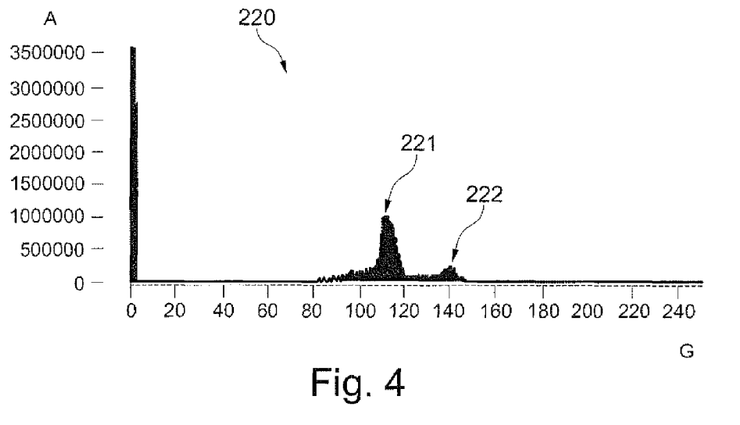
FIG. 4 shows a histogram, which illustrates the frequencies of radiation intensities of the transmission image of FIG. 3.
Figure 5:
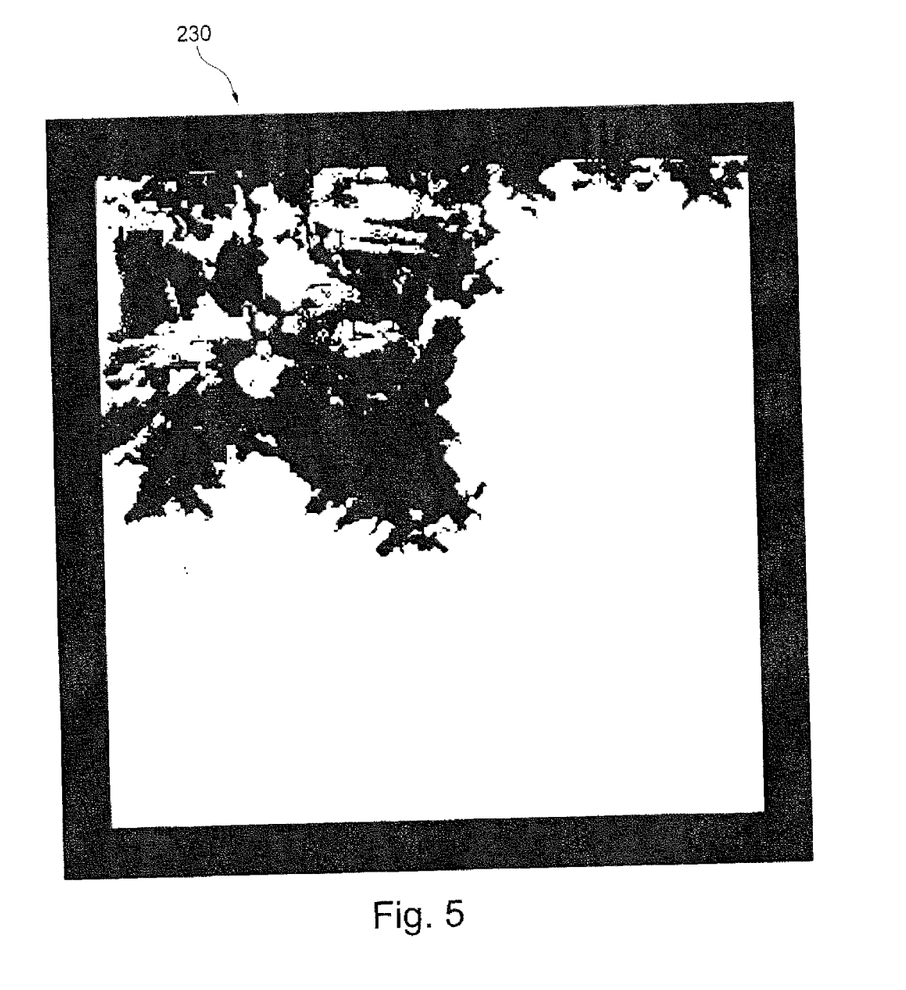
FIG. 5 shows an image of the substrate corresponding to FIG. 3, in which regions with a 100-crystal orientation are highlighted.

Initially, the examination or evaluation for a first silicon substrate 110 is described with the help of FIGS. 3 to 5. Therefore, as shown in FIG. 3, the infrared radiation 190 transmitted through substrate 110 and measured in a spatially resolved manner is converted into a transmission image 210. The transmission image 210 can be represented on a display device, which is associated with evaluation device 173 or which is connected to this (not represented). The transmission image 210 shows different measured radiation intensities of radiation 190 in the form of different brightnesses. The brightnesses can be illustrated in the form of greyscale values, which is indicated by dotted regions in FIG. 3 in a binary form. The different radiation intensities in transmission image 210 originate from a different attenuation or absorption of infrared radiation 190 on the main surface of the measured substrate 110, and therefore are associated with the respective existing crystal orientations.

For the analysis, additionally a frequency distribution of the different radiation intensities referring to the penetrated surface of substrate 110 can be formed, as is illustrated in FIG. 4 with the help of a histogram 220 corresponding to this. The histogram 220 can likewise be represented on the above mentioned display device 170. In the histogram 220, the frequency or the number A of different, spatially resolved, detected intensities are shown, wherein the intensities are represented as greyscale values G. Here, a greyscale value of 0 to 255 was taken as a basis. The histogram 220 has a first peak 221, and a second smaller peak 222.

By analyzing the frequency distribution or corresponding histogram 220, it is possible to determine the aggregate of the 100-crystal orientation referring to the substrate surface, with a higher speed and accuracy. Thereby, an "Inline"-use of the method is favored.

In the entire histogram 220, the frequencies of all the different radiation intensities, and hence all the crystal orientations are obtained. This frequency, which is referred to in the following as total frequency can be determined by adding up all the frequencies A of histogram 220, thus by integrating the overall frequency distribution.

Based on histogram 220, further the frequency of radiation intensities, which are associated only with the substrate regions with 100-crystal orientation, may be determined. This frequency is referred to in the following as partial frequency. The surface aggregate of the examined substrate 110 with 100-crystal orientation can therefore be determined by forming ratios from the partial frequency and the total frequency. This requires identifying specific radiation intensities concerned with the 100-crystal orientation in order to be able to define the partial frequency.

Different methods can be used for the allocation of radiation intensities to substrate regions with 100-crystal orientation. A possible reliable procedure is to carry out a calibration measurement. In the calibration measurement, a monocrystalline wire-sawn reference substrate or a part of such a substrate can be measured, in which the presence of the crystal orientation to be calibrated, thus the presence of 100-Orientation on the main surface is known or can be assumed. The measurement takes place in the above described manner with the help of device 170, in which the reference substrate is irradiated with infrared radiation 190 by means of irradiation device 171, and the transmitted infrared radiation 190 is detected with the help of detection device 172. The measured intensities based on this can be linked with the relevant crystal orientation. Based on the histogram 220, the frequencies of these radiation intensities can be added up or integrated in order to determine the partial frequency.

The calibration measurement can take place, for example in each substrate 110 to be examined, in particular, simultaneously with each substrate 110 to be examined. It is also possible to carry out calibration measurement only periodically or selectively and therefore, not in each substrate 110 to be examined.

Another possibility to associate the measured intensities of the infrared radiation 190 regions of substrate 110 with 100-crystal orientation, and based on this, to determine the partial frequency sought with the help of the frequency distribution or with the help of histogram 220 can take place automatically, while the peak values or peaks present here may be considered. For example, it may be taken as a basis that a peak associated with the crystal orientation sought is respectively displayed at the same position of the histogram 220. This applies at least in a relative sense, thus with reference to the shape of the histogram 220 or with reference to one or several other peaks. In view of the 100-crystal orientation, this is a peak at the lowermost greyscale value G, thus existing peak 221. Regions with 100-crystal orientation accordingly lead to the largest attenuation or absorption of the infrared radiation 190.

Provided that measurement of different substrates 110 is carried out respectively with the corresponding conditions of measurement (particularly same intensity of infrared radiation 190 delivered by the irradiation device 171), the relevant peaks 221 may respectively lie at the same greyscale values G. In histogram 220 of FIG. 4, these greyscale values G are in the range of 120 or 125. This is likewise the case in histogram 260 of another examined substrate 110, shown in FIG. 7 described further below.

By carrying out a peak search, particularly about the relevant intensity- or greyscale value range, a peak deconvolution process for separating peak 221, and integrating separated peak 221, the partial frequency sought can be determined in this manner. The surface aggregate of the relevant substrate 110 with 100-crystal orientation can be determined by computing the (percentages) aggregate of the partial frequency on the total frequency or by forming the ratios from the partial frequency and the total frequency.

In the presently examined substrate 110 with the transmission image 210 of FIG. 3, the determination of the partial frequency was carried out with the help of the previously described peak search, peak deconvolution process, and integration of the separated peak 221. On the basis of this, the value 77.2% was determined as the percentage aggregate of the 100-crystal orientation.

Further, it may be considered to carry out the above described calibration along with the peak based determination of the partial frequency. For instance, the calibration may be used for improving or verifying the peak search.

Apart from determining the surface aggregate, the analysis of the detected infrared radiation 190 can also be carried out, so that additionally or alternatively, a spatial distribution of the 100-crystal orientation over the surface of the examined silicon substrate 110 is determined. With reference to the presently examined substrate 110 with the transmission image 210 of FIG. 3, such a spatial distribution is illustrated by means of the modified transmission image 230 of FIG. 5. Here, the substrate regions with 100-crystal orientation are represented in white, whereas substrate regions with other crystal orientations (and a region around substrate 110) are represented in black.

The transmission image 230 of FIG. 5, which can likewise be represented on the display device of device 170 is compiled based on the transmission image 210 of FIG. 3, wherein substrate regions with 100-crystal orientation—based on the above described arrangement or linking of radiation intensities—are highlighted as compared to differently oriented substrate regions. With the help of the represented distribution, it can already be recognized in the run up, which regions of the substrate 110 are textured for the case of carrying out an alkaline etching process, i.e. 100-oriented regions presently represented in the white.

The method that can be carried out with the device 170 of FIG. 1, offers the possibility of characterizing 100-crystal orientation with a higher accuracy. In particular, the overall aggregate of 100-crystal orientation of a substrate surface can be detected. In a conventional method, a substrate to be examined is irradiated with visible light; an incident light image is generated, and only the largest surface with a uniform brightness than the region or grain with the 100-crystal orientation can be considered and measured. The aggregate of the largest grain alone is however not decisive for the efficiency of a solar cell with alkali produced texture. As it becomes clear from FIG. 5 with the help of transmission image 230 of the examined substrate 110, apart from a largest grain or substrate region with 100-crystal orientation, still more 100-oriented regions are present, which can likewise be alkaline textured.

In addition, it is merely assumed in the conventional approach that the largest grain has a 100-crystal orientation however a direct linking or association with the 100-orientation is not provided, as it takes place in the method described here with the help of the radiation intensities. Thereby, the problem is that a grain with a different crystal orientation is identified as the largest grain if necessary, whereby a wrong aggregate of 100-crystal orientation is determined. This case may occur, for example in the substrates which emerge from a peripheral zone of a silicon block.

Such a problem can be avoided based on linking of the measured radiation intensities with 100-crystal orientation used during the method of examination. In this manner, the method can be used further to reliably recognize error in supplying a wire-sawn silicon substrate 110. For instance, in view of the above described vertical wafer, a twisting of a pillar could be recognized before a wire sawing process.

Figure 6:
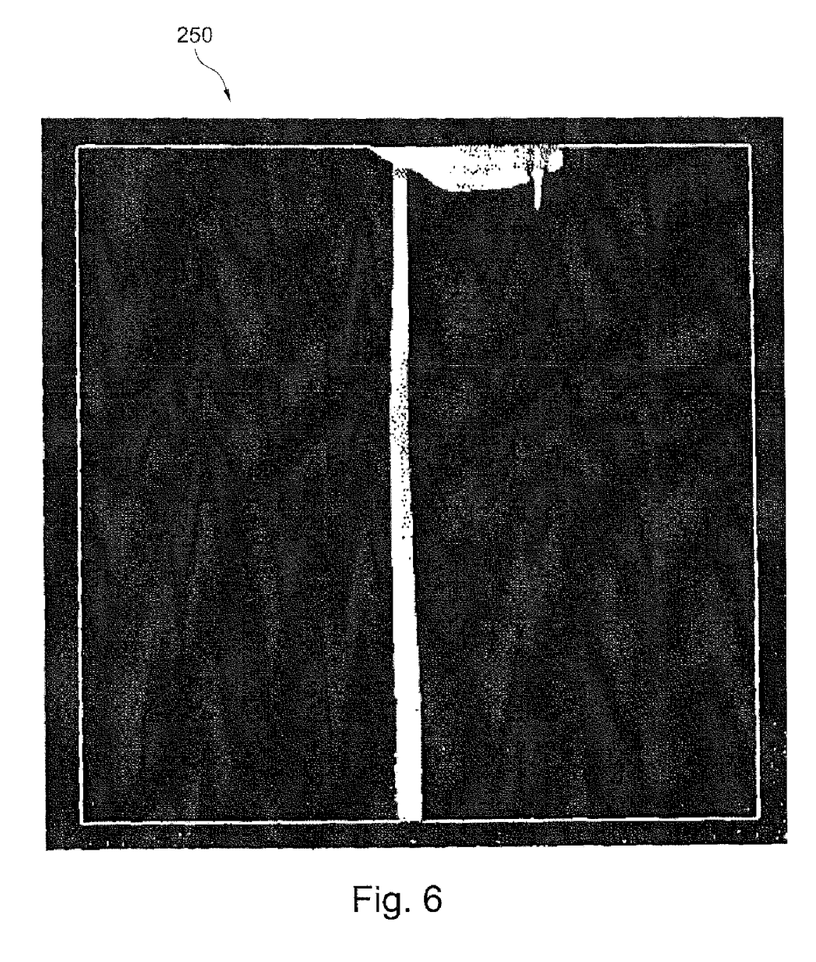
FIG. 6 shows a transmission image generated by penetrating another wire-sawn silicon substrate with the infrared radiation.
Figure 7:
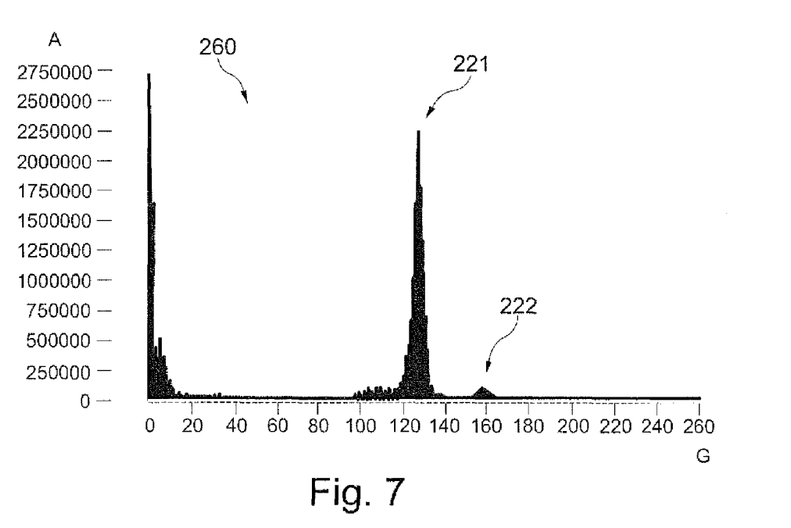
FIG. 7 shows a histogram, which illustrates the frequencies of radiation intensities of the transmission image of FIG. 6.
Figure 8:
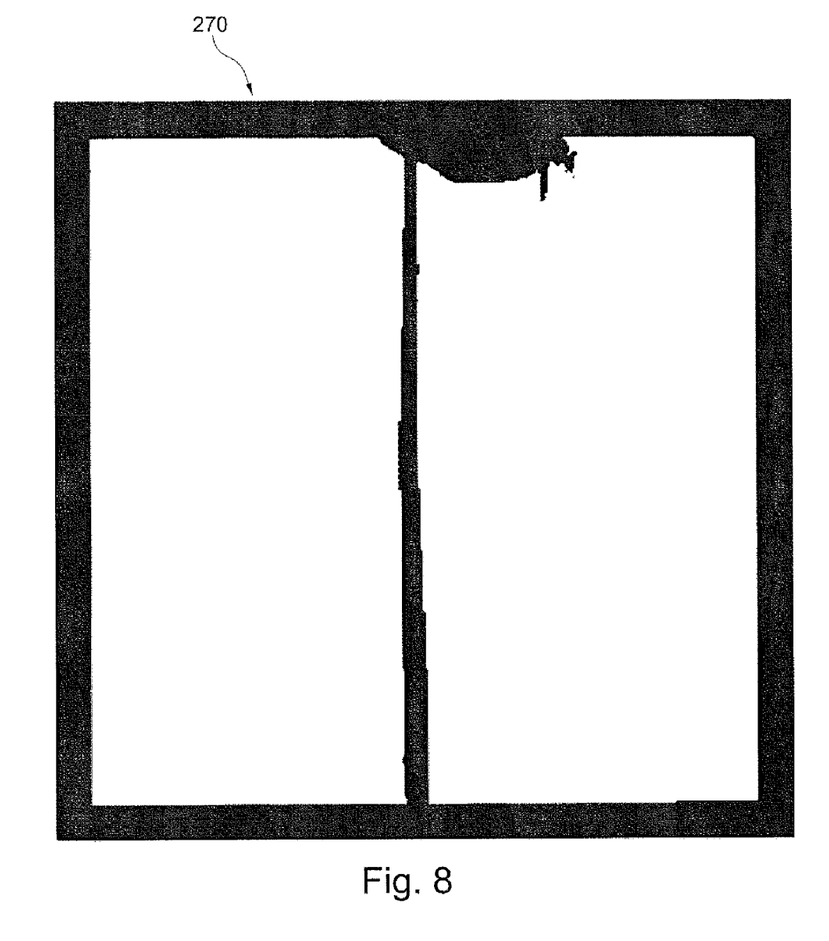
FIG. 8 shows an image of another substrate corresponding to FIG. 6, in which regions with 100-crystal orientation are highlighted.

The FIGS. 6 to 8 illustrate the analysis of a second wire-sawn silicon substrate 110 that can be carried out with the evaluation device 173. Thereby, the same steps as in the analysis described with the help of FIGS. 3 to 5 can be carried out. With reference to the details, which refer to similar type of or corresponding components and features, possible advantages etc., thus the above description is referred to.

FIG. 6 shows a transmission image of this substrate 110, which was obtained by transforming the spatially resolved, detected, transmitted infrared radiation 190 again. Here, different radiation intensities are illustrated in the form of different grayscale values (indicated in FIG. 6 with dotted regions in binary form).

FIG. 7 shows the histogram 260 associated with this, which illustrates the frequency distribution of the detected different radiation intensities applied on the penetrated surface of substrate 110. The histogram 260 again has a first peak 221, and a smaller second peak 222.

The frequency distribution or histogram 260 can be used in the same manner for determining the aggregate of 100-crystal orientation applied on the surface of the examined substrate 110. By adding up all the frequencies A of the histogram 260, thus by integrating the overall frequency distribution, the total frequency applied on all the crystal orientations can be determined. By determining the partial frequency of radiation intensities, which are merely linked with the substrate regions with 100-crystal orientation, and which form the ratios from the partial frequency and the total frequency, the surface aggregate with 100-crystal orientation can be detected.

This may take place based on a calibration measurement in order to link the measured radiation intensities with 100- crystal orientation. The partial frequency can be determined by integrating the frequencies A of these radiation intensities in histogram 260, In addition, the determination of partial frequency takes place automatically with the help of histogram 260, in which peak 221 with the lowest grayscale values G is considered. By carrying out a peak search, presently again around the grayscale region at 120, a peak deconvolution process for separating peak 221, and integrating separated peak 221, the partial frequency sought can be determined.

In the substrate 110 with transmission image 210 of FIG. 6, the determination of partial frequency can be carried out with the previously described methods (peak search, peak deconvolution process, integration of the separated peak 221). Based on this, the value 95.6% was determined as percentage aggregate of the 100-crystal orientation.

Even in second substrate 110, based on the transmission image 250 of FIG. 6 and association of radiation intensities with the substrate regions having 100-crystal orientation, a modified transmission image 270 was compiled, which is represented in FIG. 8. The transmission image 270 shows the substrate regions with 100-crystal orientation highlighted in white as compared to differently oriented substrate regions, and hence the distribution of 100-crystal orientation over the substrate surface.

With the help of the transmission image 270 of FIG. 8, the advantage of the method of examination described here as compared with the conventional approach (measuring the largest seed in the incident light) is again made clear. The shown substrate 110 has two relatively large, separated from each other substrate regions or grains with 100-crystal orientation. This may be caused, for example, based on a seed joint or twin growth. Carrying out the conventional method would have the consequence that only one of this grain to be considered, and thereby to determine a very small aggregate of the 100-crystal orientation.

The method of examination carried out with device 170 of FIG. 1 can be used, for instance in order to classify the wire-sawn silicon substrate 110 and to define further processing as a result of the same. This is described in more details in the following with the help of the flow diagram of a method for manufacturing a solar cell 100 shown in FIG. 9. Additionally, such a solar cell 100 is partially illustrated in FIG. 10.

Figure 9:
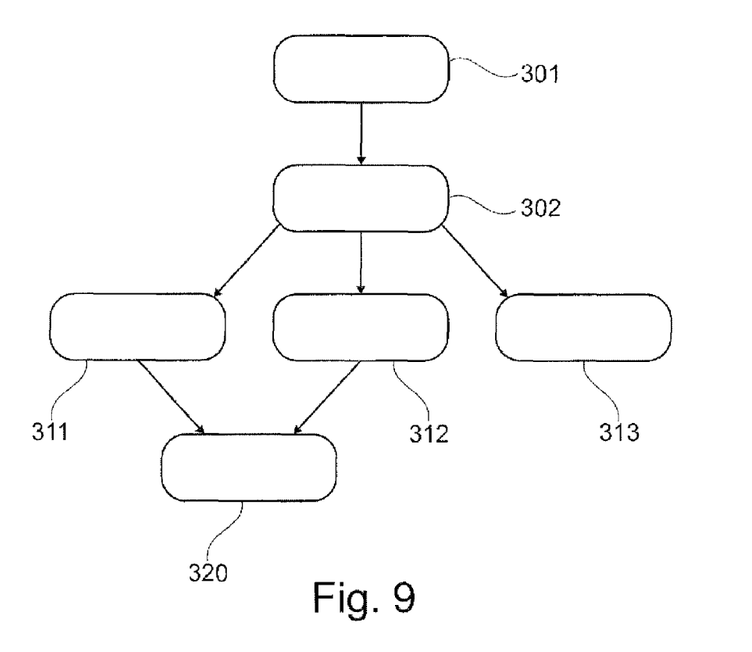
FIG. 9 shows a flow diagram of a method for manufacturing a solar cell.

During the manufacturing method, in a step 301, a wire-sawn silicon substrate 110 is supplied. For this purpose, the above described process, i.e. carrying out a Quasi-Mono process for producing a (predominantly) monocrystalline silicon block and cutting of the same by wire sawing can be carried out.

In another step 302, wire-sawn silicon substrate 110 as described above with the help of device 170, is subjected to an examination. Here, the aggregates of the 100-crystal orientation and/or their spatial distribution over the substrate surface can be determined. Depending on the examination, the substrate 110 can be classified and further processing of substrate 110 can be defined accordingly.

In the exemplary flow diagram of FIG. 9, a division into three different classes is provided. The division can take place, for example by a comparison of the detected aggregate of the 100-crystal orientation with one or multiple limiting values, and by considering the spatial distribution.

With a higher aggregate of 100-crystal orientation over a first predefined limiting value (for instance, 80% surface aggregate) and a spatial distribution classified as good, for example an allocation of substrate 110 to a first class may take place, in which an alkaline texturing of the substrate 110 takes place (step 311). With an aggregate of 100-crystal orientation below the first predefined limiting value and/or with the presence of a spatial distribution classified as poor, an allocation of the substrate 110 to a second class takes place, in which an acidic texturing of the substrate 110 takes place (step 312). In addition, it is possible within the scope of the examination that it is defined that the aggregate of 100-crystal orientation is below a second (smaller) limiting value or that the spatial distribution is evaluated as relatively poor. This leads to an allocation of the substrate 110 to a third class, in which substrate 110 is sorted out (step 313).

The above described classification merely serves as the exemplary explanation and therefore can be modified if required. In particular, it is conceivable to provide more than three classes, so that for instance, substrate 110 provided for acidic texturing can be divided in different classes. In the same manner, this can be considered for substrate 110 provided for alkaline texturing.

After the alkaline or acidic texturing of substrate 110 (not sorted out), in which a saw damage can be removed simultaneously, further processes can be carried out for completing the solar cell 100 partially represented in FIG. 10. These processes are summarized in a step 320 in the flow diagram of FIG. 9.

This includes forming a p-n junction in the silicon substrate 110, whereby a structure made of a base 116 and an emitter 115 is present. Within the scope of the step 320, the (textured) front side 111 of substrate 110 over which an irradiation of the solar cell 100 can take place, is additionally provided with an anti-reflection coating 121. In addition, the solar cell 100 is configured with contact structures. This includes finger type front side contacts 131 on the front side 111, which extend through the anti-reflection coating 121 up to substrate 110. A flat rear side contact 112 is configured on the oppositely located rear side 112 of substrate 110.

The embodiments explained with the help of figures represent the preferred or exemplary embodiments of the invention. Apart from the described and depicted embodiments, further embodiments are conceivable, which may include further variations or combinations of features.

For example, it is possible to replace the above numerical figures (for example for size of the used grayscale values, to the grayscale value region for peak 221, to a limiting value for the selection of a texturing process, etc.) by other information. Further, for manufacturing a solar cell 100, further processes other than the above described processes may be carried out, and a solar cell 100 may have further structures other than the above described structures, or also a construction diverging from FIG. 10.

In addition, it may be considered to characterize a different crystal orientation than the 100-crystal orientation of a wire-sawn silicon substrate 110 with the help of a detected, transmitted infrared radiation 190. Here, it can likewise be provided to determine a surface aggregate and/or a spatial distribution of this crystal orientation according to the above demonstrated approaches. In particular, it may be provided to compile a frequency distribution of measured radiation intensities, to compute the total frequency distribution by integrating the total frequency distribution, to determine (for instance by a peak search, peak deconvolution process and integration of the frequencies of the peak) a partial frequency of radiation intensities related with the relevant crystal orientation, and to form the ratio from the partial frequency and total frequency. Based on the analysis, even here, the further processing of substrate 110 or sorting out of the same can be defined.

It is further possible to characterize several different crystal orientations according to the above approaches.

In addition, it is referred to the possibility of carrying out the examination of a wire-sawn substrate 110, to recognize any error while providing substrate 110. The mentioned recognition of twisting of a pillar in vertical wafer falls under this. It is further possible to employ the method of examination, for example for improving an underlying crystallization- or casting process.

This case may be considered, for example for wire-sawn polycrystalline silicon substrate, which can likewise be examined according to the above approaches. Here, it may be considered to characterize 111-crystal orientation or to determine their aggregate on the substrate surface. The 111-crystal orientation can be expressed, for example as peak with the highest radiation intensities of the detected infrared radiation 190 (grayscale values) in a frequency distribution or a histogram corresponding to this. Here, in the same manner, a partial frequency of the 111-crystal orientation may be determined (for instance by peak search, peak deconvolution process, integration of the separated peak), and can be substituted in relation to the total frequency (sum or integral of frequencies of all the radiation intensities), in order to determine the aggregate of the 111-crystal orientation.

In addition, it was pointed out that the device 170 outlined in FIG. 1 may relate to a device which can be employed for examining defects of a wire-sawn silicon substrate 110 with infrared radiation 190 in the transmitted light method. Here, the evaluation device 173 can be configured for generating inter alia transmission images of the examined substrate 110 for illustrating crystal defects, to compute defect densities, etc. The method of examination described here for characterizing a defined crystal orientation can be integrated in this respect, as additional functionality in the device 170 or in its evaluation device 173.

LIST OF REFERENCE NUMERALS

100 Solar cell
110 Substrate
111 Front side
112 Rear side
115 Base
116 Emitter
121 Anti-reflection coating
131 Front side contact
132 Rear side contact
170 Device
171 Irradiation device
172 Detection device
173 Evaluation device
190 Infrared radiation
201, 202 Method step
203 Method step
210 Transmission image
220 Histogram
221, 222 Peak
230 Transmission image
250 Transmission image
260 Histogram
270 Transmission image
301, 302 Method step
311, 312 Method step
313, 320 Method step
A Number/Frequency
G Grayscale value

The invention claimed is:

1. Method for manufacturing a solar cell, wherein a wire-sawn silicon substrate is provided that is selected by carrying out the steps of:
    irradiating the silicon substrate with an infrared radiation having a wavelength within the range of 800 nm to 1200 nm;
    detecting the infrared radiation transmitted through the silicon substrate;
    analyzing the detected infrared radiation to determine a crystal orientation of the silicon substrate; and
    determining a percentage of the surface of the silicon substrate having the crystal orientation,
    wherein depending on the selection of the silicon substrate, one of the following step is carried out:
        forming a surface texture of the silicon substrate by carrying out an alkaline etching process;
        forming a surface texture of the silicon substrate by carrying out an acidic etching process; or
        sorting out the silicon substrate.

2. Method according to claim 1, wherein a frequency distribution related to a surface of the silicon substrate is formed from different intensities of the detected infrared radiation.

3. Method according to claim 1, wherein:
    a total frequency distribution of different intensities of the detected infrared radiation related to a surface of the silicon substrate is determined,
    a further frequency of intensities of the detected infrared radiation is determined, which is associated to regions of the silicon substrate with the crystal orientation, and
    a ratio is formed from the further frequency and the total frequency.

4. Method according to claim 1, wherein an association is established between the crystal orientation and the intensities of the detected infrared radiation.

5. Method according to claim 4, wherein the association is established based on a peak value in a frequency distribution of different intensities of the detected infrared radiation.

6. Method according to claim 4, wherein the association is established based on a calibration measurement.

7. Method according to claim 1, wherein a spatial distribution of the crystal orientation is determined over the surface of the silicon substrate.

8. Method according to claim 1, wherein the silicon substrate includes a monocrystalline crystal structure, and wherein the crystal orientation is a 100-crystal orientation.

9. Device for selecting the silicon substrate according to claim 1, including:
    an irradiation device for irradiating a wire-sawn silicon substrate for a solar cell with an infrared radiation;
    a detection device for detecting the infrared radiation transmitted through the silicon substrate; and
    an evaluation device for analyzing the detected infrared radiation in order to determine the crystal orientation of the silicon substrate.

10. Device according to claim 9, wherein the evaluation device is configured to form a frequency distribution of different intensities of the detected infrared radiation related to a surface of the silicon substrate, and to determine the percentage of the surface of the silicon substrate with the crystal orientation based on the frequency distribution.

* * * * *